United States Patent [19]

Shores

[11] Patent Number: 4,479,393
[45] Date of Patent: Oct. 30, 1984

[54] SAMPLER FOR SLURRIES

[75] Inventor: Bobby D. Shores, Plant City, Fla.

[73] Assignee: Ben E. Jaeger, Plano, Ill.

[21] Appl. No.: 489,128

[22] Filed: Apr. 27, 1983

[51] Int. Cl.³ .............................................. G01N 1/10
[52] U.S. Cl. ................................. 73/863.82; 73/863.86
[58] Field of Search ........... 73/863.23, 863.25, 863.81, 73/863.82, 863.83, 863.84, 863.85, 863.86

[56] References Cited

U.S. PATENT DOCUMENTS

| | | | |
|---|---|---|---|
| 1,809,324 | 6/1931 | Austin | 73/863.11 |
| 2,012,836 | 8/1935 | Talbot | 73/863.86 |
| 3,383,924 | 5/1968 | Cordell | 73/863.83 |
| 3,559,491 | 2/1971 | Thoen | 73/863.24 |
| 3,747,411 | 7/1973 | McDermott | 73/863.86 |
| 3,759,087 | 9/1973 | Iwoa | 73/863.24 |
| 3,807,233 | 4/1974 | Crawford | 73/863.11 |
| 4,161,883 | 7/1979 | Laird | 73/863.24 |

*Primary Examiner*—S. Clement Swisher

*Attorney, Agent, or Firm*—Gary, Juettner & Pyle

[57] ABSTRACT

A sampler for communicating with the interior of a vessel containing a slurry under pressure extracts a sample of the slurry from the vessel and conveys the same to a point of collection. The sampler includes a conduit having an inlet for communication with the interior of the vessel and an outlet to the exterior of the vessel, and a valve for selectively establishing and interrupting communication between the conduit inlet and the interior of the vessel. When communication is established, a sample of slurry flows into the inlet, through the conduit and to the outlet for collection, and when communication is interrupted a source of flushing liquid is coupled with the inlet to flush the conduit clean of residual sampled slurry. By virtue of introduction of flushing liquid through the conduit when slurry is not being sampled, residual slurry is prevented from settling out and/or hardening in the conduit and clogging the sampler.

19 Claims, 2 Drawing Figures

SAMPLER FOR SLURRIES

BACKGROUND OF THE INVENTION

The present invention relates to apparatus for extracting samples of product from flow lines or tanks, and in particular to an apparatus which is specially adapted for extracting samples of a slurry from a flow line or tank in which the slurry is maintained under pressure.

Various manufacturing operations require that the immediate or overall composition of a material flowing through a pipe or conduit be monitored. Such monitoring ordinarily is accomplished with apparatus denoted as samplers, which take samples of material from the main body thereof. When a composite sample of the material is required, the sampler may be operated to withdraw a series of small amounts of the material as it passes a sampling point. The individual samples are collected, and represent a composite of the total volume of material.

Other uses for samplers are in on-line analysis applications in which the immediate composition of a material must be determined. For this application, the individual samples of material are not collected as a composite sample, but instead are separately analyzed.

To obtain the samples, some samplers continuously divert streams of material from the flow lines or tanks, and from the diverted streams the samples are removed in various ways. Attempts to withdraw small quantities directly from pipes or tanks, however, have presented many problems not altogether satisfactorily solved. For example, where material receiving holes or slots in samplers are adapted to be extended directly into a pipe, sampled material can build up in such holes and slots and either block the same or contaminate subsequent samples.

Heretofore samplers of the general type have been used to obtain samples of thin or relatively nonviscous liquids which readily flow through the samplers for collection. In recent years, however, a need has arisen to sample materials which are viscous and/or tend to settle out, for example slurries. Conventional samplers do not perform satisfactorily when used to sample such highly viscous liquids or slurries, since the materials are too thick to completely flow through and out of the samplers for collection, and tend to settle out and harden in the samplers and clog the same.

One type of sampler that has been used to obtain samples of a slurry flowing through a pipe comprises a hollow stem which is extendable into and out of the pipe to present an inlet port in the stem to the flow. When the stem is extended into the pipe, slurry flows into the inlet port, through the stem and out of an outlet port from the stem for collection. Since it often happens that the slurry is not homogeneous, the stem may be extended fully across the pipe and then retracted, whereby a cross sectional sample of the slurry is obtained. However, a problem encountered is that when the stem is retracted, residual sampled material remaining in the stem tends to settle out and/or harden, which can contaminate the next sample or clog the stem and completely disable the sampler.

OBJECTS OF THE INVENTION

An object of the present invention is to provide a sampler for withdrawing samples of a slurry directly from a pipe or a tank in which the slurry is maintained under pressure.

Another object is to provide such a sampler which is flushed clean of sampled material at the end of each sampling cycle, so that the sampler cannot become clogged or contaminated by sampled material.

A further object is to provide such a sampler which is suited for automatic operation at selected intervals to obtain composite samples of the material.

SUMMARY OF THE INVENTION

In accordance with the present invention, apparatus for obtaining samples of a product from a vessel containing the product under pressure comprises a conduit having an inlet for communication with the interior of the vessel and an outlet to the exterior of the vessel, and valve means for selectively establishing and interrupting communication between said inlet and the interior of the vessel, whereby when communication is established a sample of product flows into said inlet, through said conduit and to said conduit outlet for collection. Means are also provided for introducing a flushing liquid into said conduit inlet when said valve means interrupts communication, thereby to flush said conduit clean of sampled product and prevent clogging of said conduit by any residual material that might otherwise remain therein.

The foregoing and other objects, advantages and features of the invention will become apparent upon a consideration of the following detailed description, when taken in conjunction with the accompanying drawings.

DETAILED DESCRIPTION

Figure 1:
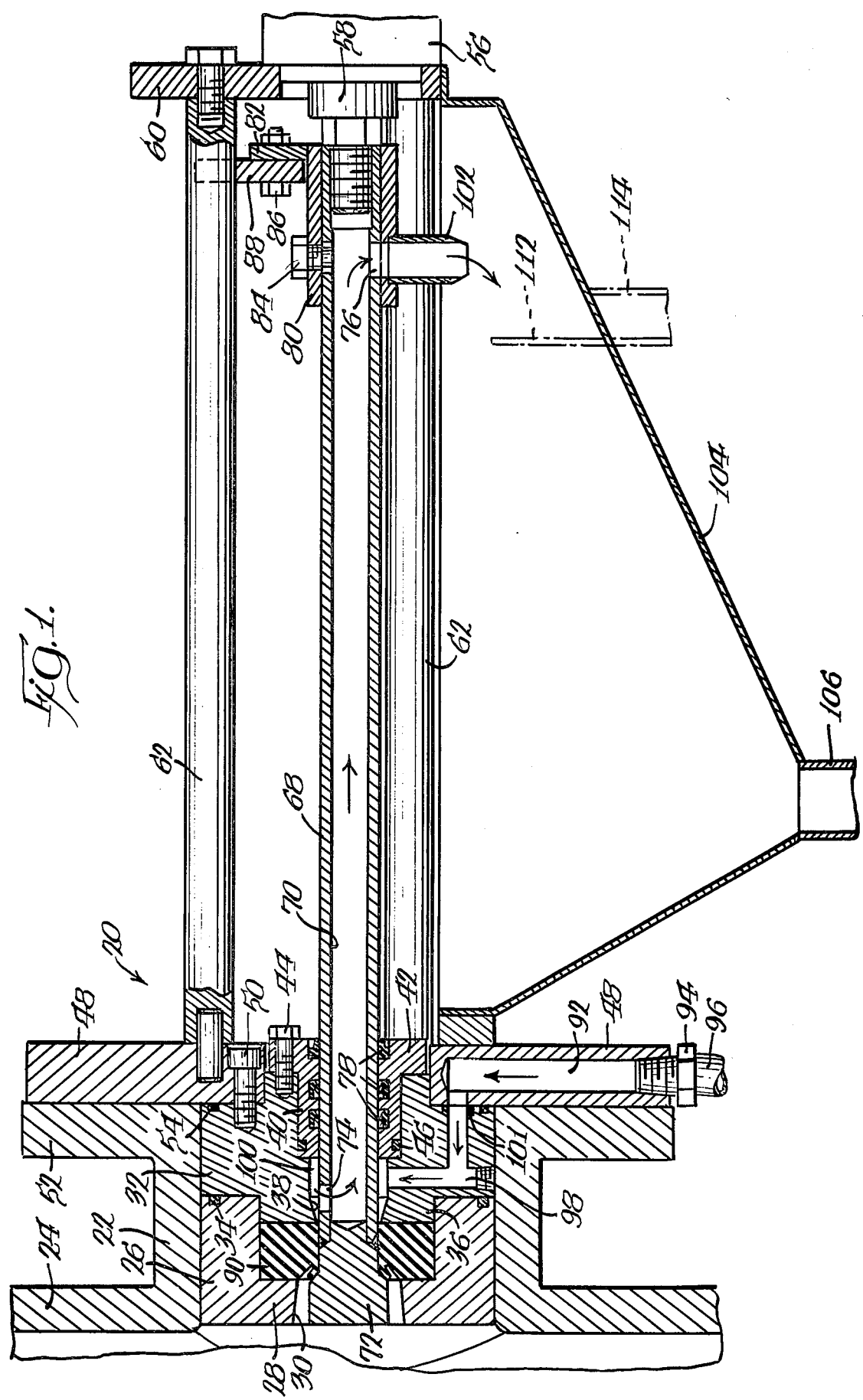
FIG. 1 is a side elevation view, partly in cross section, illustrating the structural details of a preferred embodiment of sampler for obtaining a sample of slurry from a main body thereof in which the slurry is under pressure, and for directing the sample to a point of collection, showing a plunger of the sampler withdrawn to a position whereat it may be flushed clean of any sampled material therein.
Figure 2:
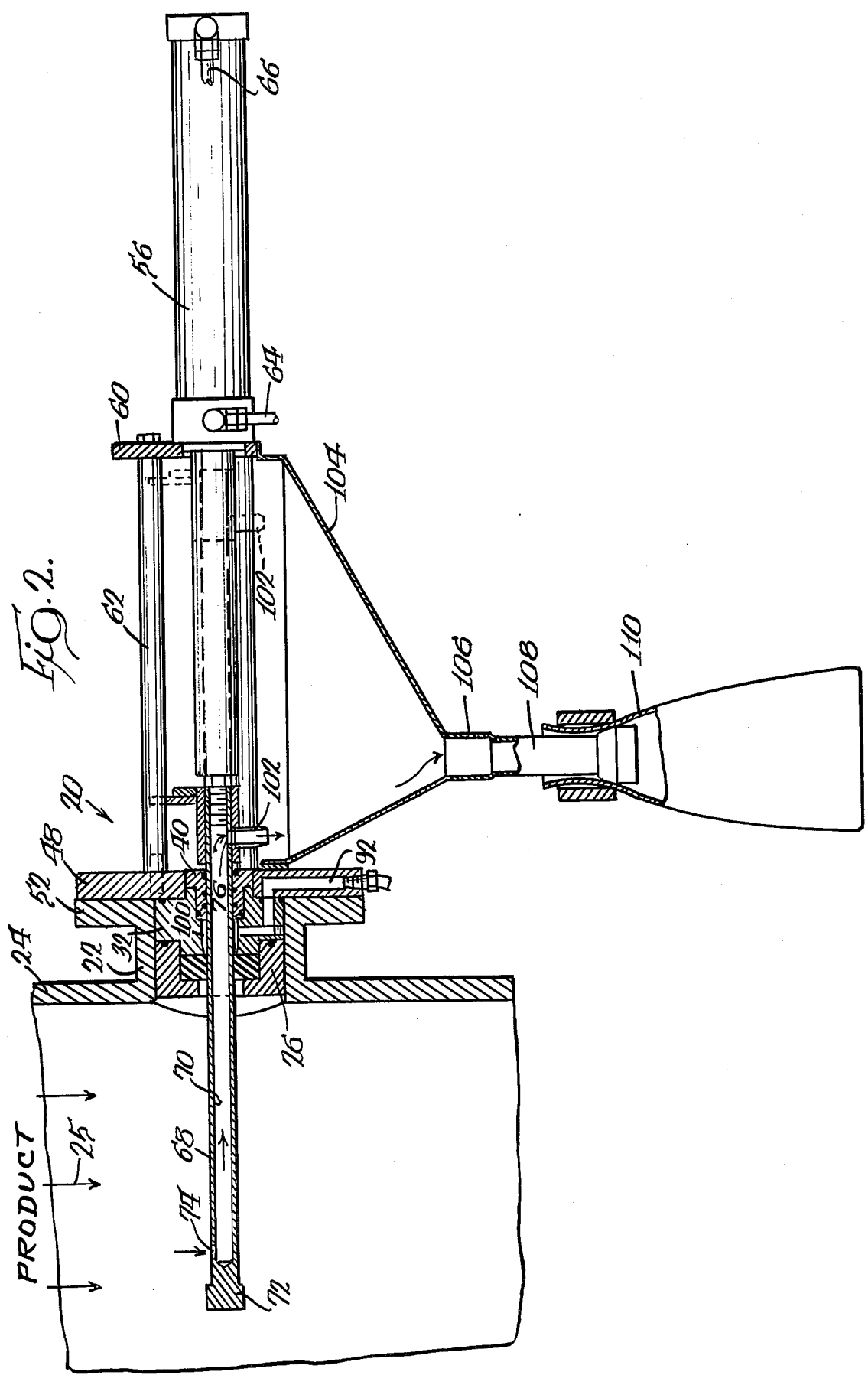
FIG. 2 is similar to FIG. 1, and shows the plunger extended into the main body of slurry for obtaining a sample thereof and conveying the same to a point of collection.

Referring to the drawings, there is indicated generally at 20 a sampler structured in accordance with the teachings of the invention. The sampler is adapted for connection with an access line 22 to a conduit or pipe 24 in which is conveyed a slurry under pressure, for example mineral particulates entrained in water and flowing in the direction indicated by arrows 25. The sampler has a hollow stem or plunger which is extendable into the pipe for receiving a sample of slurry through an inlet opening therein and for conveying the slurry therethrough to a collection point, and retractable at the end of the sampling operation to move the inlet to interior of the sampler for introduction of flushing fluid therein to cleanse the plunger of sampled material. The sampler may be cyclically actuated by pneumatic or electric motor means so that the collected material represents a composite sample of material flowing through the pipe, and a plurality of seals prevent leakage of slurry to exterior of the sampler.

More particularly, the sampler has a forward body portion which includes an annular ring 26 received and sealed within the access line 22, and a radially inwardly extending annular flange 28 at the forward end of the ring defines a passage 30 therethrough. An annular housing 32 is received and sealed within the access line rearwardly of the annular ring, and the ring and housing are fastened together by any suitable means (not shown). An annular seal 34 between the ring and housing effects a fluid tight connection therebetween and an inner, annular and axial extension 36 of the housing extends partially into the annular ring and defines with the housing a passage 38 coaxial with the passage 30.

The passage 38 has a reduced diameter at its forward end and an increased diameter at its rearward end in which is received an axial portion of a tubular sleeve 40 having a rearward radially outwardly extending annular flange 42. One or more fasteners 44 connect the flange with the housing 32, and an annular seal 46 provides a fluid tight connection between the housing and sleeve. To fasten the sampler head portion to and within the access line 22, a rearward annular mounting flange 48 is connected with a rearward face of the housing by fasteners 50 and extends across an outer annular flange 52 of the access line. An annular seal 54 forms a fluid tight connection between the flange 48 and the housing and a plurality of fasteners (not shown) connect the flanges 48 and 52 to mount the head portion on and in the access line.

A motor means for operating the sampler 20 includes an air cylinder 56, having a piston rod 58, supported rearwardly of the sampler head portion on a plate 60 carried at the ends of a plurality of rods 62 extending between the plate and head portion. The air cylinder has a forward air inlet 64 and a rearward air inlet 66 on opposite sides of a piston (not shown) therein, whereby introduction of air at the inlet 64 moves the piston and piston rod rearwardly or rightwardly (as shown in the drawings) while introduction of air at the inlet 66 moves the piston and piston rod forwardly or leftwardly.

The sampling portion of the sampler includes a hollow cylindrical plunger, conduit or stem 68 having a longitudinal passage 70 therethrough. A rearward end of the plunger is threadably connected with and closed by the forward end of the piston rod 58 and a forward end of the plunger carries and is closed by a cap 72. A sample material inlet port 74 is formed radially through the plunger just rearwardly of the cap and a sample material outlet port 76 is formed radially through the plunger just forwardly of the piston rod.

The portion of the plunger 68 forwardly of the outlet port 76 is reciprocated by the air cylinder 56 within the passages through the ring 26, housing 32 and sleeve 40, and the sleeve carries within its passage three annular seals 78 for effecting a sliding seal with the plunger. To facilitate guiding the plunger during reciprocation and to prevent it from rotating within the passages through the forward body portion, a sleeve 80 having an upstanding post 82 is secured to the rearward end of the plunger about the outlet port by a fastener 84. Connected to the post by a fastener 86 and extending upwardly therefrom is a guide arm 88 which has a U-shaped opening in its upper end in which the rod 62 is received. Thus, as the plunger reciprocates, movement of the guide arm along the rod prevents the plunger from rotating and maintains the inlet port 74 in a predetermined orientation with respect to the direction of product flow in the line 24.

To form a seal at the forward end of the sampler 20 to prevent leakage of slurry from the pipe 24 around the plunger 68, a forward annular seal 90 is provided within the recess in the annular ring 26 forwardly of the housing 32 and about the plunger 68 and cap 72. The seal effects a sliding seal with the plunger during reciprocation as well as a sealed connection with a rearward portion of the cap 72 upon retraction of the plunger, whereby slurry within the conduit is substantially prevented from leaking outwardly of the sampler. The seal is advantageously of polyurethane because of the ease by which it may be formed and its resistance to abrasion by particulate matter in the slurry, although any other material suitable for the purpose may be used.

As earlier mentioned, the sampler is characterized in that it may be flushed clean of residual sampled material after each sampling cycle, and for the purpose a passage 92 formed through the annular mounting flange 48 connects through a fitting 94 and a hose 96 with a source of flushing fluid (not shown) under pressure, for example a supply of water. The passage 92 communicates with a passage 98 through the housing 32, which in turn exits into an annular chamber 100 defined by an enlarged medial portion of the housing passage 38 about the plunger 68 and between the tubular sleeve 40 and forward seal 90. An annular seal 101 forms a fluid tight connection between the passages 92 and 98, and the arrangement is such that when the plunger is fully retracted the inlet port 74 is brought into communication with the chamber for a flow of water through the inlet port and the plunger passage 70 and out of the outlet port 76 to clean the plunger.

The remainder of the sampler comprises means for collecting samples, and to that end a tubular spout 102 extends downwardly from a passage through the sleeve 80 in communication with the plunger outlet port 76. Beneath the spout is an elongate trough 104 which extends along the entirety of the length of travel of the spout with the plunger. An outlet 106 at a lower end of the trough communicates through a tube 108 with a sample material collection container 110, which may comprise a porous bag accommodating escape therefrom of both the liquid in which is entrained particulate matter of the sampled slurry and of the flushing liquid. Should the sampler be a reasonable distance above the collection container, the trough and tube may be replaced by a flexible hose extending between the spout and container.

In operation of the sampler 20 to obtain a sample of slurry flowing through the conduit 24, air is applied at the inlet 66 to the air cylinder 56 to drive the plunger 68 leftwardly or forwardly to move the cap 72, the plunger and the sample material inlet port 74 into the pipe 24 perpendicularly to the direction of slurry flow. The sample material inlet port is usually formed through the plunger to face or oppose the direction of flow, although depending upon the nature of the product to be sampled other orientations of the port may enable more representative samples to be obtained, and has a size at least three times as great as the maximum particle size in the slurry to minimize clogging. Thus, the pressure of slurry flowing in the pipe forces a sample of slurry to enter the inlet port and flow through the plunger passage 70 and out of the outlet port 76 for collection.

Ordinarily, the plunger 68 would be extended fully across and then retracted from the pipe, so that a cross sectional sample of slurry enters the inlet port for collection, and a typical time period for extension and retraction is about one second. However, the plunger may be extended any selected distance into the pipe, and for the purpose a reversing valve (not shown) is adjustably positionable to be contacted by the guide arm 88 when the plunger has been extended a selected amount, thereby to control the amount of outward extension of the plunger. Upon being contacted, the reversing valve immediately causes the cylinder 56 to begin retracting the plunger without any dwell of the plunger in its extended position, which ensures that a representative product sample is obtained. Also, it is understood that by controlling the time for which the plunger is extended into the pipe, together with the size of the flow areas through the plunger, selected and substantially constant sample sizes may be obtained. Consequently, a number of individual samples of slurry may be collected, which then represent a composite of the total volume of slurry flowing past the sampling point during the sampling period.

To prevent slurry from leaking out of the sampler around the plunger 68 when the plunger is extended into the pipe 24, the plunger and rearward end of the cap 72 have substantially equal diameters, whereby the seal 90 seals with the plunger. Also, although flushing water introduced into the chamber 100 rearwardly of the seal ordinarily is at a relatively low pressure with respect to the pressure of the slurry in the pipe, if desired or necessary its pressure may be selected to be about ten percent greater than that of the slurry, so that the pressure of water in the chamber aids in resisting any flow of slurry past the seal, while at the same time the seal prevents any substantial flow of water from the sampler into the pipe.

When the plunger 68 has been extended into the pipe 24 to the point whereat the guide arm 88 contacts the reversing valve, air is immediately introduced at the air cylinder inlet 64 to withdraw the plunger from the pipe until the cap 72 again seats against the seal 90. This ends the basic sampling cycle, and with conventional samplers of the general type, when the sample inlet port is no longer exposed to the flow of slurry, residual slurry remaining in the plunger passage tends to settle out and/or harden as the entraining fluid drains therefrom, which can contaminate the next sample and/or completely clog and disable the sampler. However, with the sampler of the invention, when the plunger is retracted and the cap 72 moves against the seal 90, the sample material inlet port 74 is moved into communication with the chamber 100, whereupon flushing liquid in the chamber flows into the port, through the plunger passage 70 and out of the outlet port 76 to clean the same of any slurry therein. Thus, no residual slurry remains in the plunger to clog it or its inlet and outlet ports or to contaminate the next sample, and the flushing liquid simply flows out of the porous collection container 110, so that the solid remaining in the container are a true representation of those in the slurry sampled. It is understood, of course, that the particular flushing liquid used is chosen to be compatible with the entraining liquid for the solids in the slurry.

To the extent described, flushing liquid mixes with collected samples, which may not always be desirable. Accordingly, to avoid mixing advantage may be taken of the fact that when the plunger 68 is fully retracted, the plunger inlet port 74 is spaced a predetermined distance inwardly of the forward end of the seal 90, so that during initial extension and final retraction of the plunger through the predetermined distance the port is sealed off from product in the line. The movement of the plunger during which the port is sealed off from product is followed by the outlet conduit 102, and may be used to separate product samples from flushing liquid by providing, as shown in phantom lines in FIG. 1, a wall 112 in the trough 104 to separate the same into a product sample receiving portion to the left of and a flushing liquid receiving portion to the right of the wall. The wall is positioned so that upon extension of the plunger the conduit is moved to a position leftwardly of the wall by the time the plunger inlet port is exposed to product in the line, and upon retraction of the plunger the conduit is moved to a position rightwardly of the wall by the time the inlet port is exposed to flushing liquid within the chamber 100, and an outlet 114 accommodates a flow of flushing liquid and residual slurry from the trough to the right of the wall. Thus, flushing liquid and residual slurry may be maintained separate from collected samples to ensure the integrity of sampled material.

The invention thus provides an improved sampler for slurries, which utilizes the natural pressures of the slurry to be sampled to move the sample material through the sampler for collection. The sampler may be flushed clean of residual slurry remaining therein at the end of each sampling cycle, and if desired the pressure of the flushing liquid may be adjusted to control any leakage of slurry through the sampler. Consequently, the sampler may be operated in a leakproof manner and without the difficulties heretofore encountered as a result of settling or hardening of sampled material between sampling cycles and/or contamination of subsequent samples.

While embodiments of the invention have been described in detail, various modifications and other embodiments thereof may be devised by one skilled in the art without departing from the spirit and scope of the invention, as defined in the appended claims. For example, although the invention has been described as being particularly adapted for use in the sampling of slurries, it could just as readily be used with relatively viscous or nonviscous materials of a type which would tend to remain in or cling to a sampler between sampling operations.

What is claimed is:

1. Apparatus for obtaining samples of product from a vessel containing the product, comprising a conduit having an inlet for communication with the interior of the vessel and an outlet; valve means operable to establish and interrupt communication between the interior of the vessel and said inlet, whereby when communication is established a sample of product from the vessel flows through said inlet into said conduit and, through said conduit and to and through said outlet; and means for introducing flushing liquid through said inlet and into said conduit when said valve means interrupts communication between the interior of the vessel and said inlet to flush any residual sampled product from said conduit.

2. Apparatus for obtaining samples of product from a vessel containing the product, comprising a conduit having an inlet for communication with the interior of the vessel and an outlet; valve means operable to establish and interrupt communication between the interior of the vessel and said inlet, whereby when communication is established a sample of product from the vessel flows into said inlet, through said conduit and to and through said outlet; and means for introducing flushing liquid into said conduit when said valve means interrupts communication between the interior of the vessel and said inlet to flush any residual sampled product from said conduit, wherein said introducing means introduces flushing liquid into said conduit inlet when said valve means interrupts communication between the interior of the vessel and said inlet, and including means for receiving the samples of product and flushing liquid flowing through said conduit outlet, said means for receiving including a porous container which permits liquids to drain therefrom while retaining solids therein.

3. Apparatus for obtaining samples of product from a vessel containing the product, comprising a conduit having an inlet for communication with the interior of the vessel and an outlet; valve means operable to establish and interrupt communication between the interior of the vessel and said inlet, whereby when communication is established a sample of product from the vessel flows into said inlet, through said conduit and to and through said outlet; and means for introducing flushing liquid into said conduit when said valve means interrupts communication between the interior of the vessel and said inlet to flush any residual sampled product from said conduit, and including means for separately receiving the samples of product and the flushing liquid, whereby product samples are not contaminated by flushing liquid.

4. Apparatus for obtaining samples of product from a vessel containing the product under pressure, comprising a housing having a bore for communication at a forward end thereof with the interior of the vessel; a tubular plunger in said bore and reciprocable therein to move a forward end of said plunger toward and away from the interior of the vessel, said plunger having an inlet port toward said forward end thereof and an outlet port; valve means for establishing communication between said inlet port and the interior of the vessel when said plunger is moved toward the interior of the vessel for a flow of a sample of product through said inlet port into said plunger and, through said plunger and to and through said outlet port, and for interrupting communication between said inlet port and the interior of the vessel when said plunger is moved away from the interior of the vessel; and means for introducing flushing liquid through said inlet port and into said plunger to clean said plunger of any residual sampled product remaining therein when said plunger is moved away from the interior of the vessel and communication is interrupted between said inlet port and the interior of the vessel.

5. Sampling apparatus as in claim 4, wherein a forwardmost end of said tubular plunger is closed, said valve means includes forward seal means for forming a seal between said plunger and a forward end of said housing bore, and said inlet port is formed through said plunger toward but rearwardly of said forwardmost end for a flow of product therethrough when said plunger is moved toward the interior of the vessel to move said inlet port forwardly of said forward seal means.

6. Apparatus for obtaining samples of product from a vessel containing the product under pressure, comprising a housing having a bore for communication at a forward end thereof with the interior of the vessel; a tubular plunger in said bore and reciprocable therein to move a forward end of said plunger toward and away from the interior of the vessel, said plunger having an inlet port toward said forward end thereof and an outlet port; valve means for establishing communication between said inlet port and the interior of the vessel when said plunger is moved toward the interior of the vessel for a flow of a sample of product into said inlet port, through said plunger and to and through said outlet port, and for interrupting communication between said inlet port and the interior of the vessel when said plunger is moved away from the interior of the vessel; and means for introducing flushing liquid into said plunger to clean said plunger of any residual sampled product remaining therein when said plunger is moved away from the interior of the vessel and communication is interrupted between said inlet port and the interior of the vessel, wherein a forwardmost end of said tubular plunger is closed, said valve means includes forward seal means for forming a seal between said plunger and a forward end of said housing bore, said inlet port is formed through said plunger toward but rearwardly of said forwardmost end for a flow of product therethrough when said plunger is moved toward the interior of the vessel to move said inlet port forwardly of said forward seal means, and said introducing means includes a chamber in said housing bore rearwardly of said forward seal means and means for supplying flushing liquid under pressure into said chamber, and said plunger inlet port moves into communication with said chamber when said plunger is moved away from the interior of the vessel.

7. Sampling apparatus as in claim 6, including rearward seal means in said bore rearwardly of said chamber, said forward and rearward seal means forming sliding seals with said plunger and impeding leakage of product and flushing liquid through said housing bore and around said plunger.

8. Sampling apparatus as in claim 6, wherein said chamber comprises an annular recess in said bore.

9. Apparatus for obtaining samples of product from a vessel containing the product under pressure, comprising a housing having a bore for communication at a forward end thereof with the interior of the vessel; a tubular plunger in said bore and reciprocable therein to move a forward end of said plunger toward and away from the interior of the vessel, said plunger having an inlet port toward said forward end thereof and an outlet port; valve means for establishing communication between said inlet port and the interior of the vessel when said plunger is moved toward the interior of the vessel for a flow of a sample of product into said inlet port, through said plunger and to and through said outlet port, and for interrupting communication between said inlet port and the interior of the vessel when said plunger is moved away from the interior of the vessel; and means for introducing flushing liquid into said plunger to clean said plunger of any residual sampled product remaining therein when said plunger is moved away from the interior of the vessel and communication is interrupted between said inlet port and the interior of the vessel, wherein a forwardmost end of said tubular plunger is closed, said valve means includes forward seal means for forming a seal between said plunger and a forward end of said housing bore, and said inlet port is formed through said plunger toward but rearwardly of said forwardmost end for a flow of product therethrough when said plunger is moved toward the interior of the vessel to move said inlet port forwardly of said forward seal means, and wherein the vessel is a pipe through which product flows under pressure, said forward end of said plunger is extendable toward the interior of the pipe generally perpendicular to the direction of product flow and said inlet port faces generally against the direction of product flow.

10. Apparatus for obtaining samples of product from a vessel containing the product under pressure, comprising a housing having a bore for communication at a forward end thereof with the interior of the vessel; a tubular plunger in said bore and reciprocable therein to move a forward end of said plunger toward and away from the interior of the vessel, said plunger having an inlet port toward said forward end thereof and an outlet port; valve means for establishing communication between said inlet port and the interior of the vessel when said plunger is moved toward the interior of the vessel for a flow of a sample of product into said inlet port, through said plunger and to and through said outlet port, and for interrupting communication between said inlet port and the interior of the vessel when said plunger is moved away from the interior of the vessel; and means for introducing flushing liquid into said plunger to clean said plunger of any residual sampled product remaining therein when said plunger is moved away from the interior of the vessel and communication is interrupted between said inlet port and the interior of the vessel, wherein a forwardmost end of said tubular plunger is closed, said valve means includes forward seal means for forming a seal between said plunger and a forward end of said housing bore, and said inlet port is formed through said plunger toward but rearwardly of said forwardmost end for a flow of product therethrough when said plunger is moved toward the interior of the vessel to move said inlet port forwardly of said forward seal means, and wherein said forward seal means comprises a seal of polyurethane material and said closed forwardmost end of said plunger comprises a cap having a surface which moves against and seals with said polyurethane seal when said plunger is moved away from the interior of the vessel.

11. Sampling apparatus as in claim 6, including motor means for reciprocating said plunger in said bore to move said plunger toward and away from the interior of the vessel.

12. Sampling apparatus as in claim 11, wherein said plunger extends rearwardly out of said housing bore and said motor means includes an air cylinder having a piston rod connected with a rearward end of said plunger for reciprocating said plunger.

13. Sampling apparatus as in claim 6, wherein a rearwardmost end of said plunger is closed and said outlet port is formed through said plunger toward but forwardly of said rearwardmost end.

14. Sampling apparatus as in claim 13, including a collection trough extending beneath said outlet port generally coextensive with the travel thereof as said plunger reciprocates for receiving product and flushing liquid flowing therefrom.

15. Sampling apparatus as in claim 14, wherein said collection trough has an outlet therefrom, and including a container connected with said collection trough outlet for receiving both product samples flowing through said plunger and flushing liquid introduced into said plunger, said container accommodating leakage of liquids therefrom while maintaining particulate matter therein.

16. Apparatus for obtaining samples of product from a vessel containing the product under pressure, comprising a housing having a bore for communication at a forward end thereof with the interior of the vessel; a tubular plunger in said bore and reciprocable therein to move a forward end of said plunger toward and away from the interior of the vessel, said plunger having an inlet port toward said forward end thereof and an outlet port; valve means for establishing communication between said inlet port and the interior of the vessel when said plunger is moved toward the interior of the vessel for a flow of a sample of product into said inlet port, through said plunger and to and through said outlet port, and for interrupting communication between said inlet port and the interior of the vessel when said plunger is moved away from the interior of the vessel; and means for introducing flushing liquid into said plunger to clean said plunger of any residual sampled product remaining therein when said plunger is moved away from the interior of the vessel and communication is interrupted between said inlet port and the interior of the vessel, wherein a forwardmost end of said tubular plunger is closed, said valve means includes forward seal means for forming a seal between said plunger and a forward end of said housing bore, and said inlet port is formed through said plunger toward but rearwardly of said forwardmost end for a flow of product therethrough when said plunger is moved toward the interior of the vessel to move said inlet port forwardly of said forward seal means, wherein a rearwardmost end of said plunger is closed and said outlet port is formed through said plunger toward but forwardly of said rearwardmost end, and including a collection trough extending beneath said outlet port generally coextensive with the travel thereof as said plunger reciprocates for receiving product and flushing liquid flowing therefrom, and means dividing said trough into a product sample receiving portion which is beneath said outlet port when communication is established between said inlet port and the interior of the vessel and a flushing liquid receiving portion which is beneath said outlet port when communication is interrupted between said inlet port and the interior of the vessel and flushing liquid is being introduced into said plunger, whereby sampled product is maintained separate from and not contaminated by flushing liquid.

17. Apparatus for obtaining samples of product from a vessel containing the product under pressure, comprising a housing having a bore for communication at a forward end thereof with the interior of the vessel; a tubular plunger in said bore and reciprocable therein to move a forward end of said plunger toward and away from the interior of the vessel, said plunger having an inlet port toward said forward end thereof and an outlet port; valve means for establishing communication between said inlet port and the interior of the vessel when said plunger is moved toward the interior of the vessel for a flow of a sample of product into said inlet port, through said plunger and to and through said outlet port, and for interrupting communication between said inlet port and the interior of the vessel when said plunger is moved away from the interior of the vessel; and means for introducing flushing liquid into said plunger to clean said plunger of any residual sampled product remaining therein when said plunger is moved away from the interior of the vessel and communication is interrupted between said inlet port and the interior of the vessel, wherein a forwardmost end of said tubular plunger is closed, said valve means includes forward seal means for forming a seal between said plunger and a forward end of said housing bore, said inlet port is formed through said plunger toward but rearwardly of said forwardmost end for a flow of product therethrough when said plunger is moved toward the interior of the vessel to move said inlet port forward of said forward seal means, and a rearwardmost end of said plunger is closed and said outlet port is formed through said plunger toward but forwardly of said rearwardmost end, and including means for separately receiving the samples of product and the flushing liquid flowing out of said outlet port, whereby product samples are not contaminated by flushing liquid.

18. Sampling apparatus as in claim 6, including a cap at and closing a forwardmost end of said plunger and an annular seal in said housing bore toward said forward end thereof for effecting a sliding seal with said plunger, wherein said plunger inlet port is formed through said plunger toward but rearwardly of said cap, said valve means comprises said cap, said plunger forwardly of said inlet port and said annular seal, said cap seals against said annular seal when said plunger is moved away from the interior of the vessel, and said introducing means includes a chamber in said housing bore rearwardly of said annular seal and means for introducing flushing liquid under pressure into said chamber, said plunger inlet port moving rearwardly of said annular seal and into communication with said chamber when said plunger is moved away from the interior of the vessel, whereby when said inlet port is in communication with said chamber flushing liquid flows into said inlet port and thence through said plunger to said outlet port for cleaning said plunger of any residual sampled product remaining therein.

19. Sampling apparatus as in claim 18, wherein said introducing means introduces flushing liquid at a pressure which is greater than the pressure of product in the vessel, whereby the pressure of flushing liquid in said chamber assists said annular seal in preventing leakage of product from the vessel through said bore and around said plunger.

* * * * *